United States Patent
Chidambaram et al.

(10) Patent No.: US 11,672,807 B1
(45) Date of Patent: Jun. 13, 2023

(54) ORAL TESTOSTERONE NON-UNDECANOATE THERAPY

(71) Applicant: Lipocine Inc., Salt Lake City, UT (US)

(72) Inventors: Nachiappan Chidambaram, Sandy, UT (US); Satish K. Nachaegari, Holladay, UT (US); Mahesh V. Patel, Salt Lake City, UT (US); Kilyoung Kim, West Jordan, UT (US)

( * ) Notice: Subject to any disclaimer, the term of this patent is extended or adjusted under 35 U.S.C. 154(b) by 278 days.

(21) Appl. No.: 17/132,167

(22) Filed: Dec. 23, 2020

Related U.S. Application Data

(63) Continuation of application No. 16/727,737, filed on Dec. 26, 2019, now Pat. No. 10,881,670, which is a continuation of application No. 15/828,320, filed on Nov. 30, 2017, now abandoned.

(60) Provisional application No. 62/428,317, filed on Nov. 30, 2016, provisional application No. 62/428,167, filed on Nov. 30, 2016.

(51) Int. Cl.
| | |
|---|---|
| *A61K 31/568* | (2006.01) |
| *A61K 9/00* | (2006.01) |
| *A61K 9/48* | (2006.01) |
| *A61P 5/24* | (2006.01) |

(52) U.S. Cl.
CPC .......... *A61K 31/568* (2013.01); *A61K 9/0053* (2013.01); *A61K 9/48* (2013.01); *A61P 5/24* (2018.01); *A61K 9/4858* (2013.01)

(58) Field of Classification Search
CPC ..................................................... A61K 31/568
USPC ............................................................ 514/178
See application file for complete search history.

(56) References Cited

U.S. PATENT DOCUMENTS

| | | | |
|---|---|---|---|
| 10,245,273 B2 | 4/2019 | Salameh | A61K 31/568 |
| 2013/0225544 A1 | 8/2013 | Nachaegari | A61K 31/568 |
| 2014/0288039 A1 | 9/2014 | Nachaegari | A61K 31/568 |
| 2016/0184324 A1 | 6/2016 | Patel | A61K 31/568 |
| 2016/0317553 A1 | 11/2016 | Salameh | A61K 31/568 |
| 2018/0153905 A1 | 6/2018 | Chidambaram | A61K 31/568 |
| 2020/0222426 A1 | 7/2020 | Chidambaram | A61K 31/568 |

FOREIGN PATENT DOCUMENTS

| | | | | |
|---|---|---|---|---|
| WO | WO2018102618 | 6/2018 | ........... | A61K 31/568 |

*Primary Examiner* — Raymond J Henley, III
(74) *Attorney, Agent, or Firm* — Michael R. Schramm

(57) ABSTRACT

Disclosed are methods and compositions for testosterone replacement therapy, especially for use in administration to hypogonadal males. The methods and compositions employ a fixed dose dosing regimen that does not require titration or dose adjustments and that can provide a therapeutically effective amount of a non-undecanoate testosterone ester while avoiding unacceptably high testosterone levels.

53 Claims, No Drawings

ORAL TESTOSTERONE NON-UNDECANOATE THERAPY

CROSS-REFERENCE TO RELATED APPLICATIONS

This application is a continuation of and claims priority to U.S. nonprovisional patent application Ser. No. 16/727,737, filed Dec. 26, 2019 and schedule to issue as U.S. Pat. No. 10,881,670 on Jan. 5, 2021, which is a continuation of and claims priority to U.S. nonprovisional patent application Ser. No. 15/828,320, filed Nov. 30, 2017 and since abandoned, which claims the benefit of U.S. provisional application Ser. No. 62/428,167 and Ser. No. 62/428,317, both filed on Nov. 30, 2016, all of which are expressly incorporated herein by reference.

BACKGROUND OF THE INVENTION

Most testosterone based pharmaceutical products on the market employ dose titration schemes to ensure that patients are safely (e.g., avoiding unacceptably high testosterone levels) and efficaciously (e.g., achieving typical eugonadal testosterone levels in hypogonadal patients). Dose titrations are typically required because different patients can absorb and metabolize testosterone based products in substantially different manners. A dose of a testosterone product for one patient that provides safe and efficacious testosterone levels may not provide safe and efficacious levels for another patient.

SUMMARY OF INVENTION

Disclosed herein is an oral testosterone therapy ("TT") dosing regimen. In a specific aspect, the TT involves oral administration of a fixed daily dose of a testosterone ester. For example, where the testosterone ester is testosterone tridecanoate (T13), a fixed dose within the range of 750-1150 mg per day (e.g., 840-1100 mg per day) of oral T13 is unexpectedly and particularly efficacious and safe for testosterone replacement therapy (these doses can be provided once-a-day or twice-a-day as a divided dose). Thus, in another example where the testosterone ester is T13, the fixed daily dose can be provided as 375-575 mg of oral T13 twice per day for a total daily dose of 750-1150 mg T13. Surprisingly, these fixed dose regimens require no dose titration to provide safe and efficacious serum testosterone levels to a substantial proportion of subjects (e.g., those needing testosterone replacement therapy). Thus, in some aspects, the fixed dose is provided as an oral pharmaceutical composition comprising a testosterone ester (e.g., testosterone tridecanoate) and a pharmaceutically acceptable carrier, for once daily, or twice daily, etc. administration, with a meal or food, to a subject (e.g., a male having a condition associated with a deficiency or absence of endogenous testosterone).

In some embodiments, specific measures can be used to determine whether or not the therapy should continue or be discontinued. For example, biomarkers such as consistency of unacceptable testosterone (T) levels from a safety or efficacy standpoint, whether hematocrit levels rise above a threshold value, whether Prostate Specific Antigen ("PSA") levels rise above a threshold value, or any other appropriate measure or marker can be used to determine whether the therapy should be discontinued.

DETAILED DESCRIPTION OF INVENTION

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an," and "the" include plural referents unless the context clearly dictates otherwise. Thus, for example, reference to "polymer" can include a plurality of such polymers.

As used herein, "AUC" refers to the area under the serum concentration-time curve.

As used herein, "AUCt" refers to the area under the serum concentration-time curve from time zero to time of last measurable concentration.

As used herein, "$C_{avg}$" refers to average serum concentration over 24 hours.

As used herein, "$C_{max}$" refers to maximum observed serum concentration per dose over dosing interval.

As used herein, "$T_{max}$" refers to the time to maximum observed serum concentration.

As used herein, "TT" refers to testosterone therapy. In a specific definition, TT means any condition wherein serum testosterone is below the normal eugonadal range, such as 300 ng/dL when measured on two separate occasions in the morning. In another definition, the TT described herein can be used to treat patients that are eugonadal (or hypogonadal) for a condition other than specifically having testosterone levels lower than 300 ng/dL. In another specific definition, TT refers to testosterone replacement therapy e.g., to treat a condition associated with a deficiency or absence of endogenous testosterone.

As used herein, "T equivalent dose" from a T13 dose is a testosterone equivalent dose that can be released from the bioreversible T13 ester. For example, 168 mg of T13 is equivalent to 100 mg of T.

As used herein, "Eugonadal range" is the typical range of serum testosterone found in patients not needing TT, normal eugonadal range, is defined as the range with an average testosterone lower limit of ~300 ng/dL and average testosterone upper limit of 1000 ng/dL. It is understood that this normal range could vary depending on the testosterone assay utilized and variability among labs due to specific assay used by individual lab and patient demographics. Therefore, the lower limit of normal eugonadal range could also be 250 ng/dL. Similarly, the upper limit of normal eugonadal range could be 1040 or 1100, or 1500 ng/dL.

As used herein, "dosing regimen" or administration regimen" can be used interchangeably and refer to specific dosing and administration of a T13 containing product. In a specific embodiment, the dosing regimen typically entails daily dose, number of pills per dose, number of doses per day, and whether or not to take with food or fasting. The dosing regimen can also provide relevant instructions regarding the above, for healthcare providers and patients, in some embodiments. Some products (but not the product described herein) involve dose titration or a dose adjustment scheme, in patients needing adjustment, based on a patient's response to the product assessed via measured T measured T levels post dosing at steady state. A practical dosing regimen is the one that is easy to comprehend for implementation. The dosing regimen of this invention is a single fixed dose dosing regimen for TT that does not need dose titration.

As used herein, "Fixed dose" refers to the same (e.g. unchanging) daily dose of testosterone tridecanoate being used for each patient throughout a therapy regimen with no dose changes. "Single," "singular" or "unitary" fixed dose means that only one fixed daily dose (e.g., as described herein elsewhere like one of 1000 mg T13 per day) of testosterone tridecanoate is prescribed to a patient. No titration needed (or without titration) means for a given patient, the daily T13 dose is not adjusted throughout the TT.

As used herein, "Discontinuation of TT" means the dosing regimen for the patient is unsuitable for TT and should be temporarily stopped until relevant markers (e.g., biomarkers, T levels, or any other suitable marker) improve or alternatively, it may be deemed that it is permanently unsuitable for TT in the patient. As used herein, "Consistently" refers to at least two or more times or occurrences as measured on two separate occasions with a least a gap of 24 hours preferably in the morning.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, "subject" or "patient" are used interchangeably and refer to a mammal that may benefit from the administration of a composition described herein. In one aspect, the mammal may be a human.

As used herein, the terms "formulation" and "composition" are used interchangeably and refer to a mixture of two or more compounds, elements, or molecules. In some aspects, the terms "formulation" and "composition" may be used to refer to a mixture of one or more active agents with a carrier or other excipients. Compositions can take nearly any physical state, including solid and/or liquid (i.e. solution). Furthermore, the term "dosage form" can include one or more formulation(s) or composition(s) provided in a form suitable for administration to a subject.

As used herein, "effective amount" refers to an amount of an ingredient which, when included in a composition, is sufficient to achieve an intended compositional or physiological effect. Thus, a "therapeutically effective amount" refers to a substantially non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Additionally, in some cases an "effective amount" or a "therapeutically effective amount" may not be achieved in a single dose. Rather, in some examples, an "effective amount" or a "therapeutically effective amount" can be achieved after administering a plurality of doses over a period of time, such as in a pre-designated dosing regimen. Further, while the achievement of therapeutic effects may be measured by a physician or other qualified medical person using evaluations known in the art, it is recognized that individual variation and response to treatments may make the achievement of therapeutic effects a subjective decision. The determination of an effective amount is well within the ordinary skill in the art of pharmaceutical and nutritional sciences as well as medicine.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 mg to about 80 mg" should also be understood to provide support for the range of "50 mg to 80 mg." Furthermore, it is to be understood that in this written description support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-2, from 1-3, from 1-4, from 2-3, from 2-4, from 2-5, from 3-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

It is noted that testosterone levels can be monitored via a variety of testosterone assays. Such testosterone assays (e.g., for serum testosterone, total testosterone, free testosterone etc.) can be performed as part of a diagnosis of hypogonadism, a treatment efficacy assessment, or discontinuation of therapy. The assays themselves can be radioimmunoassays via commercial kits, validated mass spectrometric methods, or any other suitable assay.

It is also noted that typical regulatory approval targets for TT are based on responder outcomes targeted for patients on TT such that average daily T levels ($C_{avg}$) are restored in the normal eugonadal range in at least 75% of the treated patients and no more than 15% of the patients experience maximum serum T concentrations ($C_{max}$)>1500 ng/dL. Unacceptably high serum T level is typically defined as maximum serum concentrations of >1800 ng/dL observed in a patient post dosing in the dosing interval is typically assessed by % of patients in a group that shows $C_{max}$>1800 ng/dL.

Described herein, in one embodiment, is a method of restoring testosterone levels in a patient needing testosterone therapy (TT). The method can include administering a therapeutically effective amount of a non-undecanoate testosterone ester, such as testosterone tridecanoate (TT), to the patient via an oral dosage form. The oral dosage form can be administered to the patient in a fixed dose dosing regimen. It is noted that for the sake of clarity and brevity, T13 is generally referred to in this disclosure as an example testosterone ester. These references to T13 are not intended to be particularly limiting unless otherwise specified. More broadly, references to T13 can generally refer to any suitable non-undecanoate testosterone ester.

Described herein, in one embodiment, is a method of restoring a dihydrotestosterone (DHT) to testosterone (T) ratio (DHT/T) to a normal range (e.g. 0.05-0.33) in patients needing TT. The method can include administering a therapeutically effective amount of a testosterone ester, such as T13, to a patient via an oral dosage form using a fixed dose dosing regimen. In one aspect, the fixed dose dosing regimen can include a single daily dose of a therapeutically effective amount of T13 to an individual in need of treatment. In another aspect, the fixed dose dosing regimen can include oral administration of a therapeutically effective amount of T13 once or twice per day. In one aspect, the method comprises oral administration of a therapeutically effective amount of T13 twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 750 mg to 1100 mg of T13 per day. In one aspect, the method comprises oral administration of T13 in a fixed dose dosing regimen which provides from about 375 mg to 550 mg of T13 administered twice daily. In one aspect, the method comprises oral administration of T13 in a fixed dose dosing regimen which provides from about 400 mg to 525 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method that can provide safe and effective testosterone therapy in patients needing TT with a T13-containing oral dosage form using a fixed dose dosing regimen. In one aspect, the method comprises oral administration of therapeutically effective amount of T13 to a patient in need of treatment via a single fixed dose dosing regimen. In one aspect, the method comprises oral administration of T13 twice per day in a fixed dose dosing regimen. In one aspect, the method comprises oral administration of a therapeutically effective amount of T13 once or twice per day with food. In one aspect, the method comprises oral administration of a therapeutically effective amount of T13 once or twice per day with fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 900 mg to 1100 mg of T13 administered once daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen of T13 which provides about 900-1100 mg T13 administered once daily (e.g., about 1000 mg T13 total daily dose).

Described herein, in one embodiment, is a method of restoring average testosterone levels to a normal eugonadal range in patients needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring average testosterone levels to a normal eugonadal range while avoiding unacceptably high serum testosterone levels in patients needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring average testosterone levels to a normal eugonadal range while avoiding unacceptably high testosterone levels (e.g. maximum testosterone concentration post administration>1500 ng/dL) in patients needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

In one aspect of these embodiments, ≤20% of the treated patients (e.g., in a population of patients or subjects where the population is 10 or more, 20 or more, 30 or more, 40 or more, 50 or more, 60 or more, 70 or more, 80 or more, 90 or more, or 100 or more patients or subjects) have unacceptably high testosterone levels (e.g., maximum serum testosterone concentration post administration>1500 ng/dL) when treated with an oral dosage form including a therapeutically effective amount of T13 via a fixed dose dosing regimen that does not need dose adjustment or titration and that provides≤1150 mg of T13 per day. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

In one aspect of these embodiments, ≤15% of the treated patients (e.g., in a population of patients or subjects where the populations is 10 or more, 20 or more, 30 or more, 40 or more, 50 or more, 60 or more, 70 or more, 80 or more, 90 or more or 100 or more patients or subjects) experience maximum testosterone concentration post administration>1500 ng/dL when treated with an oral dosage form including a therapeutically effective amount of T13 to a patient via a fixed dose dosing regimen that does not need dose adjustment or titration and that provides≤1150 mg daily dose of T13. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels to a normal eugonadal range while avoiding unacceptably high testosterone levels (e.g., maximum serum testosterone concentration post administration>1800 ng/dL) in ≥90% of patients (e.g., in a population of patients or subjects where the populations is 10 or more, 20 or more, 30 or more, 40 or more, 50 or more, 60 or more, 70 or more, 80 or more, 90 or more or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels to a normal eugonadal range while avoiding unacceptably high serum testosterone levels, (e.g., maximum serum testosterone concentration post administration>1800 ng/dL) in ≥95% patients (e.g., in a population of patients or subjects where the populations is 10 or more, 20 or more, 30 or more, 40 or more, 50 or more, 60 or more, 70 or more, 80 or more, 90 or more or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels to a normal eugonadal range while avoiding unacceptably high serum testosterone levels (e.g., maximum serum testosterone concentration post administration>2500 ng/dL) in patients needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing regimen of T13. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels to a normal eugonadal range while avoiding unacceptably high serum testosterone levels (e.g., maximum serum testosterone concentration post administration>2500 ng/dl) in ≥98% patients (e.g., in a population of patients or subjects where the populations is 10 or more, 20 or more, 30 or more, 40 or more, 50 or more, 60 or more, 70 or more, 80 or more, 90 or more or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a single fixed dose dosing regimen of T13. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels to a normal eugonadal range while avoiding unacceptably high serum testosterone levels (e.g., maximum serum testosterone concentration post administration>2500 ng/dl) in all patients (e.g., in a population of patients or subjects where the populations is 10 or more, 20 or more, 30 or more, 40 or more, 50 or more, 60 or more, 70 or more, 80 or more, 90 or more or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels in patients needing TT with an oral dosage form administered in a dosing regimen that does not need dose adjustment or titration and that provides at least a 750 mg of T13 per day. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a daily dose of 750 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a daily dose of 800 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a 850 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a daily dose of 900 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a daily dose of 950 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a daily dose of 975 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a 980 mg of T13 per day and wherein at least 75% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a single fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a 990 mg of T13 per day and wherein at least 80% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a 1000 mg of T13 per day and wherein at least 85% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of UT to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 once or twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring $C_{avg}$ testosterone levels to a normal range by administering T13 in an oral dosage form using a dosing regimen that does not need dose adjustment or titration and that provides at least a 1050 mg of T13 per day and wherein at least 90% of the patients (e.g., in a population of patients or subjects where the populations is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of T13 to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of from 750 mg to 1150 mg. In one aspect, the method comprises oral administration of a therapeutically effective amount of UT to a patient in need of treatment via a fixed dose dosing regimen. In one aspect, the method comprises oral administration of a therapeutically effective amount of T13 once or twice per day in a fixed dose dosing regimen of T13. In one aspect, the method comprises oral administration of a therapeutically effective amount of T13 twice per day with food or fat containing food. In one aspect, the method comprises oral administration of T13 in a single fixed dose dosing regimen which provides from about 750 mg to 1150 mg of T13 per day. In one aspect, the method comprises oral administration of T13 in a single fixed dose dosing regimen which provides from about 800 mg to 1100 mg of T13 per day. In one aspect, the method comprises oral administration of T13 in a fixed dose dosing regimen which provides from about 400 mg to 550 mg of T13 administered twice daily. In one aspect, the method comprises oral administration of T13 in a fixed dose dosing regimen which provides from about 450 mg to 550 mg of T13 administered twice daily. In one aspect, the method comprises oral administration of T13 in a fixed dose dosing regimen which provides about 500 mg T13 administered twice daily (e.g., about 1000 mg T13 total daily dose). In one aspect, the method comprises oral administration of T13 in a fixed dose dosing regimen which provides about 900-1100 mg T13 administered once daily (e.g., about 1000 mg T13 total daily dose administered once a day).

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of about 750-1150 mg.

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of about 900-1100 mg.

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of about 950-1100 mg.

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of about 1000 mg.

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of about 990-1010 mg.

Described herein, in one embodiment, is a method of restoring testosterone levels in a patient needing TT to within normal T levels while avoiding unacceptably high T levels. The method can include administering T13 via an oral dosage form using a dosing regimen that does not need a dose adjustment or titration and that provides a daily amount of T13 of about 1000 mg.

In one embodiment, an unexpected finding of these studies, as outlined in the Examples and described herein, is the surprising discovery that a TT dosing regimen including an appropriate single fixed oral dose of T13 in the range from 750 mg to 1150 mg (or 950-1050 mg) can obviate the need for a titration scheme or dose adjustment. This is unexpected since recent previous attempts to obtain regulatory approval of an oral T13 based TT were based on dose titration schemes which were thought to be needed to ensure adequate efficacy and safety of the therapy. Additionally, many marketed TTs require dose titrations or adjustment as indicated on the product's label.

While any oral dosage form can be utilized in the dosing regimen of this invention for TT, in some examples the dosage form can be a capsule comprised of pharmaceutically acceptable components. In one embodiment, the dose of T13 is 375-575 mg (e.g., as 1 capsule or 2, 3, or 4 or more capsules) administered orally two times daily for a total daily dose of T13 from 750-150 mg. The oral dosage form can be administered with food (e.g., co-administered) having at least 10 g of fat, at least 15 g of fat, at least 20 g of fat, or at least 30 g of fat, or an amount of fat within the range of 10-60 g.

The dosing regimen of this invention can include a daily dose of T13 administered as a four times per day (QID), a thrice per day (TID), a twice per day (BID), or a once per day (QD) dosing. Whatever the number of daily doses, each dose can be equally divided to provide a total daily dose of T13 between 750-1150 mg.

The oral testosterone replacement therapy described herein was discovered to be safe and efficacious. For example, it is believed that the TT described herein meets (1), (2), (3), (4), and/or (5) of the following criteria when used in a sufficient population of individuals needing such therapy (e.g., hypogonadal men):

(1) Proportion of subjects with average serum T ($C_{avg}$) within the normal range (e.g., 300-1000 ng/dL): ≥75%, 77%, 79%, 81%, 83%, 85%, 86%, 87%, 88%, 89%, 90%, 91%, 92%, 93%, 94% or 95% or more;

(2) Proportion of subjects with average serum T ($C_{avg}$) within the normal range: ≥65%, 67%, 69%, 71%, 73%, 75%, 76%, 77%, 78%, 79%, 80%, 81%, 82%, 83%, 84% or 85% or more with a lower bound 95% CI (Confidence Interval);

Proportion with maximum serum T ($C_{max}$) outside the normal range:

(3) $C_{max}$>1500 ng/dL (no greater than 15%, 16%, 17%, 18%, 19% 20%, 21%, 22%, 23%, 24% or 25%);

(4) $C_{max}$ between 1800 and 2499 ng/dL (no greater than 5% 6%, 7%, 8%, 9% or 10%); and (5) $C_{max}$≥2500 ng/dL (0%, or no greater than 1%, 2%, 3%, 4% or 5%).

In this context, a population of individuals typically refers to at least 20 individuals (e.g., in need of treatment like hypogonadal males) and preferable at least 25, 30, 35, 40, 45, 50, 55, 60, 65, 70, 75, 80, 85, 90, 95 or 100 individuals or more.

In some embodiments, testosterone concentrations (e.g., blood, serum, or plasma) can be checked periodically, e.g., 3-12 hours after the morning dose, starting as soon as one month or two weeks (or sooner) after initiating treatment with testosterone tridecanoate. When the total testosterone concentration consistently exceeds 1200, 1300, 1400, 1500, 1600, 1700, 1800, 1900, 2000, 2100, 2200, 2300, 2400 or 2500 ng/dL, therapy with testosterone tridecanoate can be discontinued as advised by trained medical personnel. If the total testosterone concentration is consistently below 300 ng/dL, an alternative treatment can be considered as advised by trained medical personnel.

In another embodiment, testosterone (e.g., blood, serum, or plasma) concentrations can be checked periodically, e.g., any time between 3-12 hours after the morning dose, starting as soon as one month after initiating treatment with testosterone tridecanoate. If the total testosterone concentration consistently exceeds 2500 ng/dL, therapy with testosterone tridecanoate can be discontinued as advised by trained medical personnel. If the total testosterone concentration is consistently below 300 ng/dL, an alternative treatment can be considered as advised by trained medical personnel. As used in this paragraph, consistently can refer to two or more times or occurrences.

In yet another embodiment, increases in hematocrit levels, reflective of increases in red blood cell mass, may require discontinuation of oral testosterone tridecanoate. Hematocrit levels can be checked prior to initiating treatment. In some examples, it can be appropriate to re-evaluate the hematocrit levels starting from 3 months after starting treatment, and then annually. In some cases, if hematocrit levels become elevated, the therapy can be discontinued until hematocrit levels decrease to an acceptable level.

Thus, in one embodiment, the dosing regimen comprises orally administering a dosage form of that comprises T13 and a carrier including a pharmaceutically acceptable additive. The pharmaceutically acceptable additives of this invention can include one or more lipophilic additives, one or more hydrophilic additives, other suitable pharmaceutically acceptable additives, or a combination thereof.

Thus, in some embodiments, orally administered testosterone tridecanoate compositions can be used in the following exemplary replacement therapies described below or previously in this specification.

In one example, a testosterone replacement therapy for a male patient having a condition associated with a deficiency or absence of endogenous testosterone can include orally administering a fixed dose of a therapeutically effective amount of testosterone tridecanoate to the patient with food.

In some examples, the fixed dose can be from 750 mg to 1150 mg T13 per day once a day (or twice a day as a divided dose (e.g., 375-575 mg administered as a divided dose)).

In some examples, the fixed dose is 800-1100 mg testosterone tridecanoate per day (or twice a day as a divided dose (e.g., 400-550 mg administered as a divided dose)).

In some examples, the fixed dose is 850-1050 mg testosterone tridecanoate per day (or twice a day as a divided dose (e.g., 425-525 mg administered as a divided dose)).

In some examples, the fixed dose is 900-1100 mg testosterone tridecanoate per day (or twice a day as a divided dose (e.g., 450-550 mg administered as a divided dose)).

In some examples, the fixed dose is 950-1050 mg testosterone tridecanoate per day (or twice a day as a divided dose (e.g., 475-525 mg administered as a divided dose)).

In some examples, the fixed dose is 975-1025 mg testosterone tridecanoate per day (or twice a day as a divided dose (e.g., 487.5-512.5 mg administered as a divided dose)).

In some examples, the fixed dose is 990-1010 mg testosterone tridecanoate per day (or twice a day as a divided dose (e.g., 495-505 mg administered as a divided dose)).

In some examples, the fixed dose is 995-1005 mg testosterone tridecanoate per day (or twice a day as a divided dose (e.g., 497.5-502.5 mg administered as a divided dose)).

In some examples, a serum testosterone level of said male is determined after initiation of therapy.

In some examples, a serum testosterone level of said male is determined after initiation of therapy wherein unacceptably high serum testosterone levels after a fixed dose administration of testosterone tridecanoate indicates that the male discontinues said therapy.

In some examples, a serum testosterone level of said male is determined after initiation of therapy wherein unacceptably low serum testosterone levels after a fixed dose administration of testosterone tridecanoate indicates that the male discontinues said therapy.

In some examples, the testosterone tridecanoate is formulated with a lipophilic surfactant, a hydrophilic surfactant, or both.

In some examples, the testosterone tridecanoate is formulated with a triglyceride.

In some examples, the testosterone tridecanoate is formulated with a fatty acid, a monoglyceride, a diglyceride, a triglyceride, a hydrophilic surfactant, a solidifying agent, or a combination thereof.

In some examples, the fixed dose is about 990 mg testosterone tridecanoate per day.

In some examples, the fixed dose is about 995 mg testosterone tridecanoate per day.

In some examples, the fixed dose is about 1000 mg testosterone tridecanoate per day.

In some examples, the fixed dose is about 1005 mg testosterone tridecanoate per day.

In some examples, the fixed dose is about 1010 mg testosterone tridecanoate per day.

In some examples, when the total serum testosterone concentration consistently exceeds 1200, 1300, 1400, 1500, 1600, 1700, 1800, 1900, 2000, 2100, 2200, 2300, 2400 or 2500 ng/dL, therapy with testosterone tridecanoate is discontinued.

In some examples, when the total serum testosterone concentration consistently exceeds 2500 ng/dL, therapy with testosterone tridecanoate is discontinued.

In some examples, when the total serum testosterone concentration consistently exceeds 2100 ng/dL, therapy with testosterone tridecanoate is discontinued.

In some examples, when the total serum testosterone concentration consistently exceeds 1800 ng/dL, therapy with testosterone tridecanoate is discontinued.

In some examples, when the total serum testosterone concentration consistently exceeds 1500 ng/dL, therapy with testosterone tridecanoate is discontinued.

In some examples, when the total serum testosterone concentration is consistently below 300 ng/dL, therapy with testosterone tridecanoate is discontinued.

In some examples, discontinuation criteria are assessed at steady state.

In some examples, discontinuation criteria are assessed at steady state by measuring serum testosterone concentrations.

In some examples, discontinuation criteria are assessed at steady state by measuring serum testosterone concentrations 1 to 12 hours after a fixed dose administration of the oral testosterone tridecanoate.

In some examples, the therapy is discontinued when the subject's hematocrit or PSA levels are unacceptably high.

In some examples, the therapy meets 1, 2, 3, 4, or 5 of the following criteria when used in a sufficient population of individuals needing such therapy:

(1) Proportion of subjects with average serum T ($C_{avg}$) within the normal range (300-1000 ng/dL): ≥75%, 77%, 79%, 81%, 83%, 85%, 86%, 87%, 88%, 89%, 90%, 91%, 92%, 93%, 94% or 95% or more;

(2) Proportion of subjects with average serum T ($C_{avg}$) within the normal range: ≥65%, 67%, 69%, 71%, 73%, 75%, 76%, 77%, 78%, 79%, 80%, 81%, 82%, 83%, 84% or 85% or more with a lower bound 95% CI (Confidence Interval);

Proportion with maximum serum T ($C_{max}$) outside the normal range:

(3) $C_{max}$>1500 ng/dL (not >15%, 16%, 17%, 18%, 19% or 20%);

(4) $C_{max}$ between 1800 and 2499 ng/dL (not >5% 6%, 7%, 8%, 9% or 10%);

(5) $C_{max}$≥2500 ng/dL (none or not >1%, 2%, 3%, 4% or 5%);

wherein a population of individuals refers to typically at least 20 individuals or at least 25, 30, 35, 40, 45, 50, 55, 60, 65, 70, 75, 80, 85, 90, 95 or 100 individuals or more.

Thus, the testosterone replacement described herein, when used with a population of male subjects, provides safe and efficacious testosterone replacement therapy.

Examples of T13 Compositions and Dosage Forms

The dosing regimens involving T13 compositions and dosage forms are exemplified below for oral TT. The compositions and dosage forms described herein can be used with oral testosterone products and particularly T13 that are suitable for oral administration. Any suitable oral unit dosage form can be used. For example, in some embodiments, the unit dosage form is a hard gelatin or soft gelatin capsule. In other embodiments, the unit dosage form is a tablet or caplet. Other suitable unit dosage forms include, but are not limited to, powder, granulate, particulate, bead, pellet, sprinkle, suspension, solution, tablet, capsule, or combinations thereof. The dosing schemes or regimens described herein can be used with oral testosterone products formulated in any suitable manner.

Typical pharmaceutical compositions of this invention are:

| Composition 1 | | |
|---|---|---|
| Ingredient Name | Composition 1 % w/w | mg/unit* |
| Testosterone Tridecanoate | 15-45 | 140-550 |
| Pharmaceutical Acceptable Carriers | 55-85 | 550-950 |
| Total | 100.0 | 700-1500 |

*The unit quantity of each ingredient of the composition can be proportionally adjusted to the quantity for any size or form of unit dosage form such as a capsule or a tablet.

| Composition 2 | |
|---|---|
| Ingredient Name | Composition 2 % w/w |
| Testosterone Tridecanoate | 15-45 |
| Pharmaceutical Acceptable Carriers    Lipophilic Additives* | 50-85 |
| Other Additives | 0-40 |
| Total | 100.0 |

*Preferred Lipophilic Additives include one or more of mono-di glycerides, vegetable oils, fatty acid, triglycerides, phytosterols, Vitamin E, lecithin, omega 3 fatty acids.

| Composition 3 | |
|---|---|
| Ingredient Name | Composition 3 % w/w |
| Testosterone Tridecanoate | 15-45 |
| Pharmaceutical Acceptable Carriers    Hydrophilic Additives* | 0-40 |
| Other Additives | 50-85 |
| Total | 100.0 |

*Preferred Hydrophilic Additives include one or more of Cremophor RH 40, Cremphor EL, Vitamin E TPGS, Tween 80, labrasol, etc.

| Composition 4 | |
|---|---|
| Ingredient Name | Composition 4 % w/w |
| Testosterone Tridecanoate | 15-45 |
| Pharmaceutical Acceptable Carriers    Lipophilic Additives | 50-85 |
| Hydrophilic Additives | 0-40 |
| Other Additives | 0-20 |
| Total | 100.0 |

The compositions of dosage forms (e.g. capsule or tablet) described herein can include a variety of pharmaceutically acceptable carriers known in the art. Non-limited examples of the pharmaceutical acceptable carriers include lipophilic additives, hydrophilic additives, other additives, and combinations thereof.

In one embodiment, the lipophilic additives include, but not limited to, lipidic solubilizers, lipophilic surfactants, and combinations thereof. The lipidic solubilizers can comprise at least about 50 wt % of the pharmaceutically acceptable carrier. Non-limiting examples of lipidic solubilizers can include triglycerides, tocopherol, tocopherol derivatives, fatty acids, fatty acid glycerides, or combinations thereof. The triglycerides can include hydrogenated soyabean oil, hydrogenated vegetable oil, corn oil, olive oil, soyabean oil, peanut oil, sesame oil, or combination thereof. In another embodiment, the fatty acids can include caprylic acid, capric acid, lauric acid, myristic acid, palmitic acid, stearic acid, richinoleic acid, arachidic acid, behenic acid, lignoceric acid, cerotic acid, myristoleic acid, palmitoleic acid, sapienic acid, oleic acid, elaidic acid, vaccenic acid, linoleic acid, γ-linoleic acid, linoeladic acid, arachidonic acid, erucic acid, or combination thereof. In an additional embodiment, the fatty acid glycerides can be monoglycerides, diglycerides, or mixtures thereof. Non-limiting examples of fatty acid glycerides that can be used in the oral pharmaceutical compositions and dosage forms of the present invention include monoglycerides and/or diglycerides derived from sources such as maize oil, poppy seed oil, safflower oil, sunflower oil, borage seed oil, peppermint oil, coconut oil, palm kernel oil, castor oil, or mixtures thereof. In one embodiment, the glyceride derivatives described in the following surfactants may be used as lipidic solubilizers as well.

In one embodiment, a surfactant is considered as a lipophilic surfactant when it has an HLB value of 10 or less. It is important to note that some lipophilic surfactants may also function as the lipidic solubilizer component of the compositions and oral dosage forms. Various lipophilic surfactants can be used including, but not limited to mono-, di-glycerides of fatty acids like glyceryl monolinoleate (e.g. MAISINE® 35-1), mono- and di glycerides of caprylic, capric acid (e.g. CAPMUL® MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. LABRAFIL® M 2125 CS), PEG-6 almond oil (e.g. LABRAFIL® M 1966 CS), PEG-6 apricot kernel oil (e.g. LABRAFIL®M 1944 CS), PEG-6 olive oil (e.g. LABRAFIL® M 1980 CS), PEG-6 peanut oil (e.g. LABRAFIL®M 1969 CS), PEG-6 hydrogenated palm kernel oil (e.g. LABRAFIL®. M 2130 BS), PEG-6 palm kernel oil (e.g. LABRAFIL® M 2130 CS), PEG-6 triolein (e.g. LABRAFIL® M 2735 CS), PEG-8 corn oil (e.g. LABRAFIL® WL 2609 BS), PEG-20 corn glycerides (e.g. CROVOL® M40), PEG-20 almond glycerides (e.g. CROVOL® A40), lipophilic polyoxyethylene-polyoxypropylene block co-polymers (e.g. PLURONIC® L92, L101, L121 etc.); propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. CAPTEX® 200), and propylene glycol dioctanoate (e.g. CAPTEX® 800), propylene glycol monocaprylate (e.g. CAPRYOL® 90); propylene glycol oleate (e.g. Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. ARLACEL® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g. Arlacel 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, cholesterol, sitosterol, phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko), and the like, and mixtures thereof.

In one embodiment, hydrophilic additives are selected from the group consisting of hydrophilic surfactant, celluloses—such as hydroxypropyl celluloses low molecular weight, low viscosity types (e.g. METHOCEL® E5, E6, E10 E15, LV100 etc. grades) and hydroxypropyl celluloses having higher molecular weight, medium to high viscosity (e.g. METHOCEL® K4M, K15M, K100M etc.); polyvinylpyrrolidones (e.g. Kollidon k17, K30 etc.); polyvinyl acetates and combinations thereof.

In further embodiment, a surfactant is considered as a hydrophilic surfactant when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 hydrogenated castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, lanosterol PEG-24 cholesterol ether (e.g. Solulan C-24, Amerchol), PEG-30 soya sterol (e.g. Nikkol BPS-30, from Nikko), PEG-25 phyto sterol (e.g. Nikkol BPSH-25 from Nikko), PEG-30 cholestanol (e.g. Nikkol DHC, from Nikko), and mixtures thereof.

In another aspect, other additives described herein in the oral dosage forms (e.g. powder, granulate, particulate, bead, pellet, sprinkle, suspension, solution, tablet, or capsule) can include binders, bufferants, diluents, disintegrants, flavors, colorants, taste-masking agents, resins, pH modifiers, lubricants, glidants, thickening agent, opacifying agent, humectants, desiccants, effervescing agents, plasticizing agents, antioxidants, solidifying agents, control release agents, and the like.

For example, a solidifying agent is a pharmaceutically acceptable additive that is in a solid physical state at room temperature. Typically solidifying agents facilitate the solidification of the pharmaceutical compositions of the present invention at temperatures around room temperature. The compositions and capsule fill of the present invention, including those with solidifying agents, can be non-liquid at standard temperature and pressure. In an aspect, the composition and capsule fill can be semi-solid or solid at standard temperature and pressure. When present, the solidifying agent can comprise from about 0.1 wt % to about 20 wt % of the pharmaceutical composition or capsule dosage form. In one embodiment, the solidifying agent can melt at a temperature of about body temperature to about 75° C. Non-limiting examples of solidifying agents include polyethylene glycols; sorbitol; gelatin; stearic acid; cetyl alcohol; cetosterayl alcohol; paraffin wax; polyvinyl alcohol; glyceryl stearates; glyceryl distearate; glyceryl monostearate; glyceryl palmitostearate; glyceryl behenate; waxes; hydrogenated castor oil; hydrogenated vegetable oil; Vit E derivatives, bees wax, microcrystalline wax; sterols; phytosterols; phytosterols fatty acid esters, cholesterol and mixtures thereof. In one embodiment, the solidifying agent includes a polyethylene glycol (PEG) having molecular weight from about 1000 to about 20,000 and their mixtures. In another embodiment the solidifying agent includes one or more selected from the group consisting of polyethylene glycol; gelatin; stearic acid; polyvinyl alcohol; glyceryl stearates; glyceryl distearate; glyceryl monostearate; glyceryl palmitostearate; hydrogenated castor oil; hydrogenated vegetable oil and cholesterol. In an additional embodiment, the solidifying agent includes Vit E tocopherol PEG 1000 succinate or derivatives of D-α-TPGS. In one embodiment, the pharmaceutical composition can be a solid at about room temperature. In yet a further embodiment, a "not dissolved" crystalline testosterone ester can act as a solidifying agent.

The oral compositions of the present invention can be formulated to take any dosage form commonly known in the pharmaceutical arts such as granules, tablet or capsule. In one embodiment, the oral pharmaceutical compositions of the present invention can be formulated as oral dosage forms such as capsules or tablets. The capsule size can be any size known in the art and can vary depending on the desired dosage amount. For instance, in one embodiment, the capsule can be a hard gelatin capsule having a fill volume of about 0.25 mL to about 1.1 mL. Similarly, in another embodiment, the capsule can be a soft gelatin capsule having a fill volume of about 0.25 mL to about 1.5 mL.

In a specific embodiment, the compositions of the current invention can be formulated in the form of granules, powder mixtures or tablets. In a specific embodiment, the testosterone ester present in the dosage form can be present in the form of nanoparticles or amorphous particles, liquid, or mixtures thereof. In another specific embodiment, the testosterone ester present in these dosage form can be present in the form of crystalline, non-crystalline or amorphous particles or a mixtures thereof having an average particle size of about 2000 nm or less, 1500 nm or less, 1000 nm, 800 nm or less, 600 nm or less, 500 nm or less, 400 nm or less, 300 nm or less, 250 nm or less, 200 nm or less, 100 nm or less, 50 nm or less, or 25 nm or less; or the average particle size of said crystalline, non-crystalline or amorphous particles or a mixtures thereof is in the range 10 nm to 2000 nm, 10 nm to 1500 nm, 10 nm to 1000 nm, 10 nm to 800 nm, 10 nm to 750 nm; 10 nm to 600 nm, 10 nm to 500 nm, 10 nm to 400 nm, 10 nm to 300 nm, 10 nm to 250 nm, 10 nm to 200 nm, or 10 nm to 100 nm.

T13 Dosage Form Examples Containing Exemplary Compositions

| | | | Example A | | | |
|---|---|---|---|---|---|---|
| | | | Dosage Form A1 | | Dosage Form A2 | |
| Ingredient Name | | | % w/w | mg/unit | % w/w | mg/unit |
| Testosterone Tridecanoate | | | 10-20 | 140-300 | 10-15 | 140-195 |
| Pharmaceutical acceptable carriers | Lipophilic additives* | e.g. Castor oil | — | — | 48-55 | 600-850 |
| | | e.g. Oleic acid | 80-90 | 900-1400 | — | — |
| | | e.g. Propylene glycol monolaurate | — | — | 30-40 | 400-600 |
| | Other additives** (e.g. antioxidant, solidifier, etc.) | | 0-10 | 0-100 | 0-12 | 0-120 |
| Total | | | 100 | 1000-1650 | 100 | 1000-1650 |

*Lipophilic additives used in these compositions (e.g. castor oil, oleic acid, and propylene glycol monolaurate) can be replaced with other lipophilic additives or combinations described in the above contexts. This can be applied to all other examples.

**Other additives exemplified as antioxidant or solidifier in these compositions can be replaced with different other additives or combinations described in the above contexts. This can be applied to all other examples.

| | | | Example B | | | | | |
|---|---|---|---|---|---|---|---|---|
| | | | Dosage Form B1 | | Dosage Form B2 | | Dosage Form B3 | |
| Ingredient Name | | | % w/w | mg/unit | % w/w | mg/unit | % w/w | mg/unit |
| Testosterone Tridecanoate | | | 13-18 | 140-200 | 25-32 | 200-300 | 18-25 | 140-300 |
| Pharmaceutical acceptable carriers | Lipophilic additives* | Mono/diglyceride 1 (e.g. Glyceryl monolinoleate) | 60-65 | 575-830 | — | — | — | — |
| | | Mono/diglyceride 2 (e.g. Glyceryl distearate) | — | — | 4-8 | 50-80 | — | — |
| | | Fatty acid1 (e.g. Oleic acid) | — | — | 50-60 | 350-550 | 45-55 | 350-800 |
| | | Fatty acid2 (e.g. Stearic acid) | — | — | 2-6 | 25-40 | — | — |
| | | Triglyceride1 (e.g. Borage oil) | — | — | — | — | 8-12 | 70-155 |
| | | Triglyceride2 (e.g. Peppermint oil) | — | — | — | — | 2-4 | 15-40 |
| | Hydrophilic additives** (e.g. Polyoxyl 40 hydrogenated castor oil) | | 13-17 | 140-210 | 2-6 | 25-40 | 14-18 | 110-250 |

-continued

| | | Example B | | | | | |
|---|---|---|---|---|---|---|---|
| | | Dosage Form B1 | | Dosage Form B2 | | Dosage Form B3 | |
| Ingredient Name | | % w/w | mg/unit | % w/w | mg/unit | % w/w | mg/unit |
| Other additives*** | Solidifiers (e.g. PEG) | 4-8 | 50-80 | — | — | — | — |
| | Antioxidant | 0-0.3 | 0-4 | 0-0.3 | 0-4 | 0-0.3 | 0-4 |
| Total | | 100 | 850-1350 | 100 | 650-1200 | 100 | 900-1550 |

*Lipophilic additives used in these compositions can be replaced with other lipophilic additives or combinations described in the above contexts. This can be applied to all other examples.
*Hydrophilic additives used in these compositions (e.g. polyoxyl 40 hydrogenated castor oil) can be replaced with other hydrophilic additives or combinations described in the above contexts. This can be applied to all other examples.
***Other additives exemplified as solidifier and antioxidant in these compositions can be replaced with different other additives or combinations described in the above contexts. This can be applied to all other examples.

| | | | Example C | | | | | |
|---|---|---|---|---|---|---|---|---|
| | | | Dosage Form C1 | | Dosage Form C2 | | Dosage Form C3 | |
| Ingredient Name | | | % w/w | mg/unit | % w/w | mg/unit | % w/w | mg/unit |
| Testosterone Tridecanoate | | | 10-15 | 140-200 | 10-15 | 140-200 | 10-15 | 140-200 |
| Pharmaceutical acceptable carriers | Lipophilic additives* | Triglyceride (e.g. Castor oil) | 22-28 | 300-450 | — | — | — | — |
| | | Fatty acid (Oleic acid) | — | — | 24-30 | 300-470 | 24-30 | 300-470 |
| | | Mono/diglyceride derivative (e.g. Propylene glycol monolaurate) | 15-18 | 200-300 | — | — | — | — |
| | | Mono/diglyceride (e.g. Glyceryl distearate) | — | — | — | — | 12-15 | 150-240 |
| | | Monoglyceride (e.g. Glyceryl monooleate) | | | 14-18 | 180-280 | 5-10 | 100-170 |
| | | Glyceride derivative (e.g. Oleoyl polyoxyl-6 glycerides) | 10-15 | 150-230 | 10-15 | 130-225 | 4-6 | 50-100 |
| | | Lipophilic surfactant (e.g. Lecithin) | 0.5-1.5 | 5-15 | 0.5-1.5 | 5-15 | 0.5-1.5 | 5-15 |
| | | Lipophilic surfactant (e.g. Phytosterol) | 1-3 | 25-40 | 1-3 | 25-40 | 1-3 | 25-40 |
| | Hydrophilic additives** | e.g. Polyoxyl 40 hydrogenated castor oil | 25-35 | 350-525 | 6-12 | 110-185 | 6-12 | 110-185 |
| | | e.g. Polysorbate 80 | — | — | 18-22 | 230-350 | 18-22 | 230-350 |
| | | e.g. D-α-tocopherol | — | — | 1-3 | 20-40 | 1-3 | 20-40 |
| | Other additives*** | Control release agent | 0.5-1.5 | 5-15 | 0.5-1.5 | 5-15 | 0.5-1.5 | 5-15 |
| | | Antioxidant | 0-0.3 | 0-1.0 | 0-0.3 | 0-1.0 | 0-0.3 | 0-10 |
| Total | | | 100 | 1000-1600 | 100 | 1000-1600 | 100 | 1000-1600 |

*Lipophilic additives used in these compositions can be replaced with other lipophilic additives or combinations described in the above contexts. This can be applied to all other compositions.
*Hydrophilic additives used in these compositions can be replaced with other hydrophilic additives or combinations described in the above contexts. This can be applied to all other compositions.
***Other additives used in these compositions can be replaced with different other additives or combinations described in the above contexts. This can be applied to all other compositions.

Non-limiting examples of dosing regimen for oral TRT with dosage forms containing compositions of this invention comprising TT are described below:

Single Fixed Dose Dosing Regimen Examples for Safety with food with at least 10 g of fat

| Category | Regimen # | T13 Dose (mg) | Cmax >1500 ng/dL <20% patients | Cmax >1500 ng/dL <15% patients | Cmax > 1800 ng/dL <10% patients | Cmax > 1800 ng/dL <5% patients | Cmax > 2500 ng/dL <2% patients | Cmax > 2500 ng/dL none of patients |
|---|---|---|---|---|---|---|---|---|
| QD | 1 | 500 | Yes | Yes | Yes | Yes | Yes | Yes |
| | 2 | 700 | Yes | Yes | Yes | Yes | Yes | Yes |
| | 3 | 750 | Yes | Yes | Yes | Yes | Yes | Yes |
| | 4 | 800 | Yes | Yes | Yes | Yes | Yes | Yes |
| | 5 | 900 | Yes | Yes | Yes | Yes | Yes | Yes |
| | 6 | 1000 | Yes | Yes | Yes | Yes | Yes | Yes |
| | 7 | 1100 | Yes | Yes | Yes | Yes | Yes | Yes |
| | 8 | 1150 | Yes | No | Yes | Yes | Yes | No |
| | 9 | 1250 | No | No | No | No | No | No |
| BID-equal dose (AM/PM) | 10 | 250/250 | Yes | Yes | Yes | Yes | Yes | Yes |
| | 11 | 350/350 | Yes | Yes | Yes | Yes | Yes | Yes |
| | 12 | 375/375 | Yes | Yes | Yes | Yes | Yes | Yes |
| | 13 | 400/400 | Yes | Yes | Yes | Yes | Yes | Yes |
| | 14 | 450/450 | Yes | Yes | Yes | Yes | Yes | Yes |
| | 15 | 500/500 | Yes | Yes | Yes | Yes | Yes | Yes |
| | 16 | 550/550 | Yes | Yes | Yes | Yes | Yes | Yes |
| | 17 | 575/575 | Yes | Yes | Yes | Yes | Yes | Yes |
| | 18 | 625/625 | Yes | Yes | Yes | Yes | Yes | Yes |

Single Fixed Dose Dosing Regimen Examples for Efficacy with food with at least 10 g of fat

| Category | Regimen # | T13 Dose (mg) | Cavg > 300 ng/dL ≥80% patients | Cavg > 300 ng/dL ≥75% patients |
|---|---|---|---|---|
| QD | 1 | 500 | No | No |
| | 2 | 700 | No | No |
| | 3 | 750 | No | Yes |
| | 4 | 800 | Yes | Yes |
| | 5 | 900 | Yes | Yes |
| | 6 | 1000 | Yes | Yes |
| | 7 | 1100 | Yes | Yes |
| | 8 | 1150 | Yes | Yes |
| | 9 | 1250 | Yes | Yes |
| BID-equal dose (AM/PM) | 10 | 250/250 | No | No |
| | 11 | 350/350 | No | No |
| | 12 | 375/375 | No | Yes |
| | 13 | 400/400 | Yes | Yes |
| | 14 | 450/450 | Yes | Yes |
| | 15 | 500/500 | Yes | Yes |
| | 16 | 550/550 | Yes | Yes |
| | 17 | 575/575 | Yes | Yes |
| | 18 | 625/625 | Yes | Yes |

Dosage Form Example B of Composition 4 with dosing regimen (Regimen #. 1-9) of dosing category BID-equal dose with daily dose range 500-1250 mg of T13 in this invention were used for a clinic study of Testosterone Therapy for hypogonadal males.

The Clinical Study is following as

This Clinical Study is a Randomized Double-Blind, Placebo-Controlled Dose Escalating Study of the Safety, Efficacy, Tolerability, and Pharmacokinetics of Testosterone Therapy in Hypogonadal Males. This clinic study was a single and multiple, ascending-dose study that was designed to determine the optimal starting, titration (if appropriate), or single fixed dose for safety and efficacy targeted by US FDA. The study also verified the time for testosterone levels to reach steady state and identified a suitable single fixed dose dosing regimen that satisfies unmet need for safety and efficacy for oral TRT.

This study was carried out with conditions of a single-center, randomized, double-blind, placebo-controlled, ascending multiple-dose, and serial-group in adult hypogonadal male subjects. The objectives of this study were:
  a) To assess the safety, efficacy, and tolerability of escalating single and multiple oral doses of T13 dosage forms in hypogonadal males
  b) To determine the pharmacokinetics (PK) of testosterone (T), DHT, TT, DHTT, and estradiol (E2) after single and multiple oral doses of TT dosage forms in hypogonadal males
  c) To identify single fixed dose dosing regimen satisfying USFDA target, not needing to titrate for restoring average serum T levels in hypogonadal males to the normal T range.

The following sections summarize the critical elements of the study and pertinent clinical pharmacology results.

The dosing regimen for this clinic study ranged from 500 mg daily dose to 1250 mg daily dose with once a day dosing. Observed pharmacokinetic parameters (T, DHT, T13, DHTT, and E2) after single and multiple oral doses of T13 dosage forms in the patients were recorded by each daily dose in the report. Further analysis to identify single fixed dose dosing regimen that does not need to titrate for safety and efficacy was carried out based on the criteria targeted by USFDA. For example, the pharmacokinetic parameters of T level after administration of dosing regimens for 1) 750 mg T13 QD and 2) 1000 mg T13 QD daily doses were measured and analyzed according to the criteria targeted by US FDA as T Cavg/day>300 ng/dL should be more than 75% of patients
1) 750 mg T13 QD dosing regimen resulted in 76.2% of patients with T Cavg/day>300 ng/dL; Cavg (±SD) for 750 mg T13 QD dose at steady state (14 days) is 352 (±41) ng/dL.
2) 1000 mg T3 QD dosing regimen resulted in 88.1% of patients with T Cavg/day>300 ng/Dl; Cavg (±SD) for 1000 mg TT QD dose at steady state (14 days) is 405 (±148) ng/dL.

T Cmax/dose<1,500 ng/dL should be more than 85% of patients
1) 750 mg T13 QD dosing regimen resulted in 99.5% of patients with T Cmax/dose<1,500 ng/dL; Cmax (±SD) for 750 mg T13 QD dose at steady state (14 days) is 822 (±254) ng/dL.
2) 1000 mg T13 QD dosing regimen resulted in 92.8% of patients with T Cmax/day<1,500 ng/Dl; Cmax (±SD) for 1000 mg T13 QD dose at steady state (14 days) is 930 (±326) ng/dL.

The overall analyzed results of this clinic study were plotted according to % of patients for safety (Cmax<1,500 ng/dL) and efficacy (Cavg>300 ng/dL) with a variety of dosing regimen. Its results are shown in the below table.

Clinical Trial Results for % Patients for the Cavg Criteria with Various Daily Dose

| Daily dose (mg) | Equivalent T Dose (mg) | % with Cavg/day > 300 ng/dL* |
|---|---|---|
| 500 | 298 | 36.3 |
| 700 | 417 | 71.5 |
| 750 | 446 | 76.2 |
| 800 | 476 | 80.0 |
| 900 | 536 | 85.0 |
| 1000 | 595 | 88.1 |
| 1100 | 655 | 90.0 |
| 1150 | 685 | 90.7 |
| 1250 | 744 | 91.6 |

*Bold letters satisfy that % patients for Cavg/day > 300 ng/dL is more than 75%.

Clinical Trial Results for % Patients for the Cmax Criteria with Various Daily Dose

| Daily dose (mg) | Equivalent T Dose (mg) | % with Cmax/dose < 1,500 ng/dL** |
|---|---|---|
| 500 | 298 | 100.0 |
| 700 | 417 | 100.0 |
| 750 | 446 | 99.5 |
| 800 | 476 | 98.8 |
| 900 | 536 | 96.7 |
| 1000 | 595 | 92.8 |
| 1100 | 655 | 85.6 |
| 1150 | 685 | 80.0 |
| 1250 | 744 | 66.8 |

*Bold letters satisfy that % patients for Cmax/dose < 1,500 ng/dL is more than 85%.

In conclusion, the single fixed dose dosing regimen of oral T13 dose with no need to titrate (or dose adjust) ranges from 750 mg daily dose to 1100 mg daily dose of T13, which satisfies US FDA T level target for safety and efficacy for testosterone replacement therapy.

What is claimed is:

1. A method of restoring serum testosterone levels to a normal eugonadal range in a male having a condition associated with a deficiency or absence of endogenous testosterone, comprising orally administering a pharmaceutical composition comprising a therapeutically effective amount of a non-undecanoate testosterone ester in a fixed dose administration regimen with food.

2. The method of claim 1, wherein said composition further comprises an additive.

3. The method of claim 1, wherein said fixed dose administration regimen provides a total daily dose of said non-undecanoate testosterone ester of at least one of 750-1150 mg, 800-1100 mg, 850-1050 mg, 900-1100 mg, 925-1075 mg, 950-1050 mg, 975-1025 mg, 985-1015 mg, 990-1010 mg, 995-1005 mg, about 750 mg, and about 1000 mg.

4. The method of claim 1, wherein said fixed dose administration regimen comprises administering said composition once or twice daily.

5. The method of claim 1, wherein said composition is in a form of at least one of a hard capsule, a soft capsule, a tablet, a caplet, a powder, a granulate, a particulate, a bead, a pellet, a sprinkle, a suspension, a solution, and a combination thereof.

6. The method of claim 1, wherein a unit dosage form of said composition comprises about 100-500 mg of said non-undecanoate testosterone ester.

7. The method of claim 1, further comprising measuring a therapy discontinuation criterion that indicates an advised discontinuation of therapy where serum testosterone (T) levels are consistently >2500 ng/dl.

8. The method of claim 1, wherein said food comprises food having a fat content of at least one of at least 10 g, at least 15 g, at least 20 g, at least 30 g, and about 10-60 g.

9. A method of restoring daily average serum testosterone ($C_{avg}$) to a normal eugonadal range in at least 75% of males in a population having a condition associated with a deficiency or absence of endogenous testosterone, comprising oral administration of an oral dosage form comprising a therapeutically effective amount of a non-undecanoate testosterone ester in a fixed dose administration regimen with food.

10. The method of claim 9, wherein said oral dosage form further comprises an additive.

11. The method of claim 9, wherein said fixed dose administration regimen provides a total daily dose of said non-undecanoate testosterone ester of at least one of 750-1150 mg, 800-1100 mg, 850-1050 mg, 900-1100 mg, 925-1075 mg, 950-1050 mg, 975-1025 mg, 985-1015 mg, 990-1010 mg, 995-1005 mg, about 750 mg, and about 1000 mg.

12. The method of claim 9, wherein said fixed dose administration regimen comprises administering said oral dosage form once or twice daily.

13. The method of claim 9, wherein said dosage form is in a form of at least one of a hard capsule, a soft capsule, a tablet, a caplet, a powder, a granulate, a particulate, a bead, a pellet, a sprinkle, a suspension, a solution, and a combination thereof.

14. The method of claim 9, wherein said therapeutically effective amount is about 100-500 mg.

15. The method of claim 9, further comprising measuring a therapy discontinuation criterion that indicates an advised discontinuation of therapy where serum T levels are consistently >2500 ng/dl.

16. The method of claim 9, wherein said food comprises food having a fat content of at least one of at least 10 g, at least 15 g, at least 20 g, at least 30 g, and about 10-60 g.

17. A method of treating a condition associated with a deficiency or absence of endogenous testosterone in a male patient, comprising orally administering a fixed dose of about 375-575 mg of a non-undecanoate testosterone ester twice daily or about 750-1150 mg of a non-undecanoate testosterone ester once daily in a fixed dose dosing regimen with food.

18. The method of claim 17, wherein said fixed dose provides a total daily dose of said non-undecanoate testosterone ester of at least one of 800-1100 mg, 850-1050 mg, 900-1100 mg, 925-1075 mg, 950-1050 mg, 975-1025 mg, 985-1015 mg, 990-1010 mg, 995-1005 mg, about 750 mg, and about 1000 mg.

19. The method of claim 17, wherein said food comprises food having a fat content of at least one of at least 10 g, at least 15 g, at least 20 g, at least 30 g, and about 10-60 g.

20. A method of treatment comprising orally administering a pharmaceutical composition comprising a therapeutically effective amount of a non-undecanoate testosterone ester in an untitrated dose administration regimen with food.

21. The method of claim 20, wherein said composition further comprises an additive.

22. The method of claim 20, wherein said untitrated dose administration regimen provides a total daily dose of said non-undecanoate testosterone ester of at least one of 750-1150 mg, 800-1100 mg, 850-1050 mg, 900-1100 mg, 925-1075 mg, 950-1050 mg, 975-1025 mg, 985-1015 mg, 990-1010 mg, 995-1005 mg, about 750 mg, and about 1000 mg.

23. The method of claim 20, wherein said untitrated dose administration regimen comprises administering said composition once or twice daily.

24. The method of claim 20, wherein said composition is in a form of at least one of a hard capsule, a soft capsule, a tablet, a caplet, a powder, a granulate, a particulate, a bead, a pellet, a sprinkle, a suspension, a solution, and a combination thereof.

25. The method of claim 20, wherein a unit dosage form of said composition comprises about 100-500 mg of said non-undecanoate testosterone ester.

26. The method of claim 20, further comprising measuring a therapy discontinuation criterion that indicates an advised discontinuation of therapy where serum testosterone (T) levels are consistently >2500 ng/dl.

27. The method of claim 20, wherein said food comprises food having a fat content of at least one of at least 10 g, at least 15 g, at least 20 g, at least 30 g, and about 10-60 g.

28. The method of claim 20, wherein said composition is administered to at least one of a eugonadal subject and a hypogonadal subject.

29. The method of claim 20, wherein said method causes daily average serum testosterone ($C_{avg}$) to be in a normal eugonadal range in at least 75% of males in a population having a condition associated with a deficiency or absence of endogenous testosterone.

30. A method of treatment comprising orally administering a fixed dose of about 375-575 mg of a non-undecanoate testosterone ester twice daily or about 750-1150 mg of a non-undecanoate testosterone ester once daily in an untitrated dose dosing regimen.

31. The method of claim 30, wherein said composition further comprises an additive.

32. The method of claim 30, wherein said untitrated dose administration regimen provides a total daily dose of said non-undecanoate testosterone ester of at least one of 800-1100 mg, 850-1050 mg, 900-1100 mg, 925-1075 mg, 950-1050 mg, 975-1025 mg, 985-1015 mg, 990-1010 mg, 995-1005 mg, about 750 mg, and about 1000 mg.

33. The method of claim 30, wherein said untitrated dose administration regimen comprises administering said composition once or twice daily.

34. The method of claim 30, wherein said composition is in a form of at least one of a hard capsule, a soft capsule, a tablet, a caplet, a powder, a granulate, a particulate, a bead, a pellet, a sprinkle, a suspension, a solution, and a combination thereof.

35. The method of claim 30, wherein a unit dosage form of said composition comprises about 100-500 mg of said non-undecanoate testosterone ester.

36. The method of claim 30, further comprising measuring a therapy discontinuation criterion that indicates an advised discontinuation of therapy where serum testosterone (T) levels are consistently >2500 ng/dl.

37. The method of claim 30, wherein said food comprises food having a fat content of at least one of at least 10 g, at least 15 g, at least 20 g, at least 30 g, and about 10-60 g.

38. The method of claim 30, wherein said composition is administered to at least one of a eugonadal subject and a hypogonadal subject.

39. The method of claim 30, wherein said method causes daily average serum testosterone ($C_{avg}$) to be in a normal eugonadal range in at least 75% of males in a population having a condition associated with a deficiency or absence of endogenous testosterone.

40. A pharmaceutical composition comprising (i) a therapeutically effective amount of a non-undecanoate testosterone ester; (ii) at least one pharmaceutically acceptable carrier; and (iii) at least one additive, wherein said non-undecanoate testosterone ester comprises about 15%-45% w/w of said composition.

41. The composition of claim 40, wherein said composition comprises at least one of a lipophilic surfactant, a hydrophilic surfactant, a solidifying agent, a fatty acid, and a combination thereof.

42. The composition of claim 41, wherein said lipophilic surfactant comprises at least one of a monoglyceride, a diglyceride, a triglyceride, and a combination thereof, and wherein said hydrophilic surfactant comprises at least one of a PEG-8 caprylic/capric glyceride, a lauroyl macrogol-32 glyceride, a stearoyl macrogol glyceride, a PEG-40 hydrogenated castor oil, a PEG-35 hydrogenated castor oil, a sodium lauryl sulfate, a sodium dioctyl sulfosuccinate, a polyethylene glycol fatty acid mono-ester mixture, a polyethylene glycol fatty acid di-ester mixture, a polysorbate 80, a polysorbate 20, a polyethylene glycol 1000 tocopherol succinate, a phytosterol, a phytosterol fatty acid ester, a lanosterol PEG-24 cholesterol ether, a PEG-30 soya sterol, a PEG-25 phyto sterol, a PEG-30 cholestanol, and a combination thereof, and wherein said solidifying agent comprises at least one of polyethylene glycol, sorbitol, gelatin, stearic acid, cetyl alcohol, cetostearyl alcohol, paraffin wax, bees wax, microcrystalline wax, polyvinyl alcohol, glyceryl stearate, glyceryl distearate, glyceryl monostearate, glyceryl palmitostearate, glyceryl behenate, hydrogenated castor oil, hydrogenated vegetable oil, a vitamin E derivative, sterol; phytosterol, a phytosterol fatty acid ester, and cholesterol, and a combination thereof, and wherein said fatty acid comprises at least one of a monoglyceride, a diglyceride, a triglyceride, and a combination thereof.

43. The composition of claim 40, wherein said composition further comprises an additive.

44. The composition of claim 40, wherein said composition comprises an untitrated dose administration regimen composition.

45. The composition of claim 40, wherein said administration composition provides a total daily dose of said non-undecanoate testosterone ester of at least one of 750-1150 mg, 800-1100 mg, 850-1050 mg, 900-1100 mg, 925-1075 mg, 950-1050 mg, 975-1025 mg, 985-1015 mg, 990-1010 mg, 995-1005 mg, about 750 mg, and about 1000 mg.

46. The composition of claim 40, wherein said composition comprises at least one of a once-a-day composition and a twice-a-day composition.

47. The composition of claim 40, wherein said composition comprises a form of at least one of a hard capsule, a soft capsule, a tablet, a caplet, a powder, a granulate, a particulate, a bead, a pellet, a sprinkle, a suspension, a solution, and a combination thereof.

48. The composition of claim 40, wherein a unit dosage form of said composition comprises about 100-500 mg of said non-undecanoate testosterone ester.

49. The composition of claim 40, wherein said composition includes a discontinuation criterion that indicates an advised discontinuation of administration of said composition where serum testosterone (T) levels are consistently >2500 ng/dl.

50. The composition of claim 40, wherein said composition comprises an administration with food composition.

51. The composition of claim 50, wherein said food comprises food having a fat content of at least one of at least 10 g, at least 15 g, at least 20 g, at least 30 g, and about 10-60 g.

52. The composition of claim 40, wherein said composition comprises an administration to at least one of a eugonadal subject and a hypogonadal subject composition.

53. The composition of claim 40, wherein administration of said composition causes daily average serum testosterone ($C_{avg}$) to be in a normal eugonadal range in at least 75% of males in a population having a condition associated with a deficiency or absence of endogenous testosterone.

* * * * *